United States Patent
Dasgupta et al.

(10) Patent No.: US 8,114,824 B1
(45) Date of Patent: Feb. 14, 2012

(54) COMPOSITIONS COMPRISING FATTY ACYL ISETHIONATE SURFACTANT PRODUCT, ALKANOYL COMPOUNDS AND TRIGLYCERIDES WITH LOW LEVEL OF HYDROGENATION

(75) Inventors: Bivash Ranjan Dasgupta, Hamden, CT (US); Prabhjyot Singh, Stratford, CT (US); Hongjie Liu, Shelton, CT (US); Rajendra Mohanlal Dave, Newark, NJ (US); Prem Chandar, Closter, NJ (US)

(73) Assignee: Conopco, Inc, Englewood Cliffs, NJ (US)

( * ) Notice: Subject to any disclaimer, the term of this patent is extended or adjusted under 35 U.S.C. 154(b) by 0 days.

(21) Appl. No.: 12/960,884

(22) Filed: Dec. 6, 2010

(51) Int. Cl.
*A61K 7/50* (2006.01)

(52) U.S. Cl. ........ 510/130; 510/156; 510/424; 510/426; 510/463; 510/499

(58) Field of Classification Search .................. None
See application file for complete search history.

(56) References Cited

U.S. PATENT DOCUMENTS

| | | | |
|---|---|---|---|
| 5,009,814 | A | 4/1991 | Kelkenberg et al. |
| 5,389,279 | A | 2/1995 | Au et al. |
| 2010/0210500 | A1 | 8/2010 | Liu et al. |
| 2011/0118162 | A1* | 5/2011 | Shiloach et al. ............. 510/123 |

OTHER PUBLICATIONS

Co-pending Application for Applicant: Tsaur et al.; U.S. Appl. No. 12/751,049, filed Mar. 31, 2010, entitled: Personal Wash Cleanser with Mild Surfactant Systems Comprising Alkoyl Glycinate and Defined Fatty Acyl.

Co-pending Application for Applicant: Tsaur et al,: U.S. Appl. No. 12/751,063, filed Mar. 31, 2010, entitled; Personal Wash Cleansers Comprising Alkoyl Glycinate Defined Fatty Acyl Isethionate Surfactant Product and Skin.

Co-pending Application for Applicant. Tsaur et al.; U.S. Appl. No. 12,751,079, filed Mar. 31, 2010, entitled Personal Wash Cleanser Comprising Defined Alkenoyl Compounds, Defined Fatty Acyl Isethionate Surfactant.

Weitz et al., *Diffusing Wave 5 Spectroscopy. Dynamic Light Scattering*, edited by W. Brown (Oxford University Press, Oxford, 1992.

Denkov et al., "*Wall Slip and Viscous Dissipation in Sheared Foams: Effect of Surface Mobility*", J. Colloids & Surfaces A 263, p. 29 (2005).

\* cited by examiner

*Primary Examiner* — Necholus Ogden, Jr.
(74) *Attorney, Agent, or Firm* — Ronald A. Koatz

(57) ABSTRACT

The present invention relates to novel composition containing specific mild surfactant system comprising fatty acyl isethionate product and alkanoyl surfactant. Addition of triglyceride of specific degree of hydrogenation permits the retention of emollient benefit while retaining also "squeaky" feel of soap and maintaining lather stability.

11 Claims, No Drawings

COMPOSITIONS COMPRISING FATTY ACYL ISETHIONATE SURFACTANT PRODUCT, ALKANOYL COMPOUNDS AND TRIGLYCERIDES WITH LOW LEVEL OF HYDROGENATION

FIELD OF THE INVENTION

The present invention relates to compositions, particularly liquid compositions comprising specific surfactant systems used in combination with triglycerides, in particular soybean oil, having low level of hydrogenation. More particularly, use of specific surfactant system provides a rheology or feel which approaches the "squeaky clean" feel of soap desired by many consumers. On the other hand, consumers also desire the sensory feel and benefit of triglyceride oil, but such benefit has been found difficult to obtain while retaining squeaky feel. Unexpectedly, applicants have found that when triglyceride oils (especially soybean oil) use relatively low levels of hydrogenation, they can be combined with specific surfactant systems, as claimed, to provide compositions which have skin feel ("squeaky feel") approaching that of cleansers made of soap instead of synthetic surfactants while retaining the emolliency benefit of the oil, all without depressing foam profile.

BACKGROUND OF THE INVENTION

It is desirable to many consumers (particularly in certain parts of the globe, e.g., Asia) to obtain, from typically milder synthetic surfactant systems, the "squeaky feel" sensation (rheology) associated with pure soap compositions. Soap compositions are of course, typically much harsher on the skin. One particular surfactant system, which is both mild and still provides a good squeaky feel sensation associated with soap, comprises a combination of fatty acyl isethionate surfactant product and alkanoyl surfactant, e.g., glycinate.

It is further desirable to add to cleansing compositions components which have an emollient effect on the skin and which preferably also do not strongly affect lather feel or longevity. Typically components which produce such an emollient effect are oils such as triglyceride oils. Unfortunately, a problem in the art has been that, when such oily emollients are used, they tend to decrease or eliminate "squeaky feel" associated with soap. They may also have impact on lather.

Quite unexpectedly, applicants have found that, in specific fatty acyl isethionate and alkanoyl systems, use of triglyceride (particularly soybean oil) having defined percentage of hydrogenation (i.e., no higher than a certain defined level of hydrogenation) permits a closer soap-like feel while retaining benefit of use of such triglyceride, all without comprising lather.

In applicants copending application, U.S. Ser. No. 12/751,049; U.S. Ser. No. 12/751,063; and U.S. Ser. No. 12/751,079, all to Tsaur, applicants disclose cleanser systems comprising the combination of fatty acyl isethionate surfactant product and alkanoyl compounds, e.g., acyl glycinate surfactants. There is no disclosure of using such compositions in combination with triglycerides (particularly soybean oil) or that, if used, the level of hydrogenation of the triglyceride should be kept below a critically defined value. There is further no recognition that such defined triglycerides (compared to those with higher levels of hydrogenation) could be used while providing a more soap-like rheology or feel ("squeaky clean"), all while being used in milder surfactant system than soap and without seriously comprising lather.

Applicants copending U.S. Ser. No. 12/371,050 to Liu, filed Feb. 13, 2009, discloses compositions comprising blends of saturated to unsaturated triglycerides. There is no disclosure in this application of the specific fatty acyl isethionate surfactant product plus acyl alkanoyl surfactant system of the subject invention and again, no recognition that triglycerides having ceiling on level of hydrogenation can provide squeaky feel rheology (in non-soap surfactant system), maintain benefits of the use of oil emollients, and not seriously comprise lather.

BRIEF SUMMARY OF THE INVENTION

Unexpectedly applicants have now found that the combination of specifically defined surfactant system and triglyceride of defined hydrogenation value (e.g., no more than a maximum level of hydrogenation) provides compositions having rheology approaching that of cleansers made of soap while retaining benefit of oil emollient. The specifically defined triglyceride also is beneficial in that it does not depress lather as would be expected from use of such oil.

In one embodiment, compositions of the invention comprise:

1) 1 to 30%, preferably 2 to 25%, more preferably 3 to 20% of a surfactant system comprising:
   a) 5 to 70% surfactant system of a fatty acyl isethionate product which product comprises 40% to 80% (of the product) fatty acyl isethionate and 15 to 50% (of the product) free fatty acid and/or fatty acid salt/soap (product may also comprise isethionate salts and traces, typically less than 2% of product, of impurities); and
   b) 20 to 85%, preferably 30 to 75% by wt. surfactant system of an alkanoyl surfactant or surfactant (e.g., alkanoyl glycinate, alkanoyl sarcosinate or mixtures thereof) wherein alkyl group on alkanoyl group is $C_8$ to $C_{20}$, preferably $C_{12}$ to $C_{16}$ straight chain alkyl; and
2) 1 to 15%, preferably 5 to 12% by wt. of triglyceride oil (e.g., soybean oil), having degree of hydrogenation (saturated single bonds in fatty acid chains of the triglyceride versus unsaturated double bonds in the fatty acid chains) of 40% or less, preferably 1 to 35%.

In a second embodiment of the invention, there is used the same surfactant system (components 1)(a) and 1)(b) above), but there can be used higher levels of triglyceride, as long as the level of hydrogenation is reduced. In this second embodiment, compositions may comprise 5 to 30% triglyceride, preferably 10 to 25%, wherein degree of hydrogenation is less than 25%, preferably less than 20%.

Use of lower levels of hydrogenation ensures that compositions will have rheology closer to that of cleansers made of soap than to that of syndet. Specifically, this rheology can be measured by calculating the slope of the line defined by change in dimensionless shearing stress over change in dimensionless shear rate for the compositions. This slope is a measure of the mobility of the interface between bubbles. Soap has a substantially immobile interface between bubbles and, thus, compositions which have measured slopes approaching that of soap would also have an immobile interface. Such immobile interface (function of slope value) is associated with the "squeaky clean" feel perceived when soap compositions are used. Consequently, slope can be used as measure of squeaky feel perception.

In addition to being associated with "squeaky" soap-like feel, minimizing level of hydrogenation also minimizes lather degeneration.

In more specific embodiments, the compositions of the invention (1) may comprise additional surfactants such as amphoterics (e.g., betaine); (2) may comprise $C_{10}$-$C_{18}$ fatty acids (e.g., lauric acid); (3) and may comprise acrylate polymers.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to personal product compositions comprising specific mild surfactant systems and triglycerides with specific degree of hydrogenation. Using specifically defined triglycerides permits the composition to have rheology closer to that of rheology of cleansers made of soap. This is observed by the fact that compositions have measured slope (referring to dimensionless shear stress on y axis and dimensionless shear rate on x axis) which approaches the slope value of a soap cleanser composition. This slope is a measure of interface mobility or immobility between bubbles and, the value of the slope measured for soap compositions is a likely indicator of "squeaky" soap-like feel observed by consumers in consumer trials.

It is a problem in the art that, when oily, emollient compounds are used, they tend to decrease or eliminate such squeaky clean feel. The invention specifically relates to compositions which, in addition to the specific surfactant system, contain triglycerides, yet retain the noted rheology which is closer to that of soap (measured, as noted by slopes as defined in the invention). Further, they are able to do so without inhibiting the lather associated with cleansing rinse.

In one embodiment, the invention relates to compositions comprising:
1) 1 to 30%, preferably 2 to 25% of a surfactant system comprising:
   a) 5 to 70% of surfactant systems of fatty acyl isethionate product comprising 40 to 80% (of the product) fatty acyl isethionate and 15 to 50% (of the product) free fatty acid and/or fatty acid soap; and
   b) 20 to 85%, preferably 30 to 75% by wt. of an alkanoyl surfactant or surfactant; and
2) 1 to 15%, preferably 5 to 12% by wt. of a triglyceride oil wherein triglyceride oil has degree of hydrogenation of 40% or less, preferably 1 to 35%.

In a second embodiment, the same surfactant system is used, but higher levels of triglyceride can be used (while retaining more soap-like feel, as well as lather) as long as level of hydrogenation is reduced. In this embodiment, composition comprises 5 to 30% triglycerides, preferably 10-25% by wt., and level of hydrogenation is less than 25%, preferably less than 20%.

One way of quantifying the fact that a smaller degree of hydrogenation of triglyceride does not significantly hinder lather (i.e., lather stability is maintained) is by measuring the transport "mean free path" ("mfp"), in millimeters, as a function of time (e.g., t=0 to t=600 seconds) using diffusing wave spectroscopy (DWS). This measures the turbidity of lather. The transport mfp is, among other things, a function of bubble size (smaller mfp signifies smaller bubble size which, in turn, is associated with lather stability). Thus, the higher the transport mfp (as generally occurs over time), the less the turbidity, the larger is the bubble size and the more is the lather is degraded. By plotting a graph of transport mfp (on y axis) versus time (x axis) over various plotted time points, one can produce curves for each composition sample. The greater the area under the plotted curve, the larger the bubbles which, as noted, is a function of greater lather degradation.

Specifically, for purposes of this invention, compositions which meet the criteria of the invention in terms of amounts of oil and degree of hydrogenation have area under curve value of less than 830, preferably 700 or less (area under curve for base composition without soybean oil is 522.5). Thus, for example, composition with surfactant system of invention as defined having 10% soybean which is 40% or less hydrogenated will measure area under curve (transport mfp versus time from 10 seconds up to 580 seconds) of less than 830, preferably 700 or less. For 20% oil loading, hydrogenation must be less than 25%, preferably less than 20% to have area under curve of less then 830, preferably 700 or less.

One requirement of the mild surfactant composition of the invention is fatty acyl isethionate product. In applicants previous application Ser. No. 12/751,049 to Tsaur et al., filed Mar. 31, 2010, for example, applicants noted how it was surprising to find that a combination of fatty acyl isethionate product and alkanoyl surfactant (such as surfactant blend of this invention) lead to enhanced mildness as measured by patch test and LCAT tests The preferred fatty acyl isethionate product comprises (in addition to other components) both pure fatty acyl isethionate surfactant (e.g., 40 to 80% of the product) as well as free fatty acid and/or fatty acid salt (e.g., 15 to 50%). In addition, greater than 20%, preferably greater than 25% of the fatty acyl isethionate and less than 45 wt. % are of chain length greater than or equal to $C_{16}$; and greater than 50%, preferably greater than 60% of the free fatty acid/soap is of chain length $C_{16}$ to $C_{20}$.

The fatty acyl isethionate surfactant component is typically prepared by the reaction of an isethionates salt such as alkali metal isethionates and an aliphatic fatty acid having 8 to 20 carbon atoms and Iodine Value (measuring degree of unsaturation) of less than 20 g, for example:

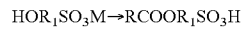

$$HOR_1SO_3M \rightarrow RCOOR_1SO_3H$$

where $R_1$ is an aliphatic hydrocarbon radical containing 2 to 4 carbons;

M is alkali metal cation or metal ion (e.g., sodium, magnesium, potassium, lithium), ammonium or substituted ammonium cation or other counterion; and R is an aliphatic hydrocarbon radical having 7 to 24, preferably 8 to 22 carbons.

Depending on the processing conditions used, the resulting fatty acyl isethionate product can be a mixture of 40 to 80% by weight of fatty acyl isethionates (which formed from the reaction) and 50 to about 15 wt. %, typically 40 to 20 wt. % of free fatty acids. In addition, product may contain isethionates salts which are present typically at levels less than 5 wt. %, and traces (less than 2 wt. %) of other impurities. Preferably, a mixture of aliphatic fatty acids is used for the preparation of commercial fatty acyl isethionates surfactants. The resulting fatty acyl isethionate surfactants (e.g., resulting from reaction of alkali metal isethionate and aliphatic fatty acid) should have more than 20 wt. %, preferably more than 25%, but no more than 40% wt., preferably 35% (on basis of fatty acyl isethionates reaction product) of fatty acyl group with 16 or greater carbon atoms to provide both lather and mildness of the resulting fatty acyl isethionate product. These longer chain fatty acyl isethionate surfactants and fatty acids, i.e. fatty acyl group and fatty acid with 16 or more carbons, form insoluble surfactant/fatty acid crystals typically in water at ambient temperatures. While not wishing to be bound by theory, it is believed that these long chain fatty acyl isethionate surfactants in the product together with free long chain fatty acids in the product contribute to the mildness of the fatty acyl isethionate product for skin cleanser applications.

Examples of commercial fatty acyl isethionate products that are particularly useful in the subject invention are DEFI flakes and Dove® cleansing bar noodles produced by Unilever. DEFI (Direct Esterification of Fatty Isethionate) flakes typically contain about 68 to 80 wt. % of sodium fatty acyl isethionate and 15 to 30 wt. % free fatty acid. More than 25 wt. % and no more than 35% of fatty acyl group of the resulting fatty acyl isethionate have 16 to 18 carbon atoms. Dove® cleansing bar noodles are mixtures of DEFI flakes described above and long chain (mainly $C_{16}$ and $C_{18}$) fatty acid and fatty soap which contain about 40 to 55 wt. % of fatty acyl isethionate and 30 to 40 wt. % of fatty acid and fatty soap. Due to the high level of long chain (16 or more carbons) fatty acyl isethionate and fatty acid, these preferred fatty acyl isethionate surfactant products are extremely mild and have very good emollient benefits to the skin.

A second required component (b) of the surfactant system is the alkanoyl surfactant or surfactants.

A preferred surfactant is salt of alkanoyl glycinate. Preferred salts include alkali metal salts of alkanoyl glycinate such as sodium cocoyl glycinate and/or alkanolamino salts such as trialkanolamine salt of glycinate.

As is well known in the art, alkanoyl is the systematic name for group:

which is also known as an acyl group. Thus, alkanoyl glycinate is the same as acyl glycinate and represents a molecule, for example, where salt of acyl group, such as for example:

(where R may be, for example, $C_8$-$C_{24}$, preferably $C_{12}$-$C_{20}$) is combined with glycine:

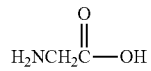

to form the alkanoyl glycinate (an amide where alkanoyl group bonds to nitrogen to form amide):

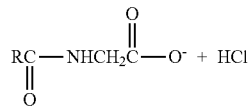

The above reaction may be conducted, for example, by an acid chloride route where R group on the acyl chloride is used to define the R group on the final alkanoyl glycinate (e.g., cocoyl glycinate if R in the acyl group is a cocoyl group).

Another preferred alkanoyl surfactant is alkanoyl, as defined above, combined with sarcosine to form alkanoyl sarcosinate (e.g., lauroyl sarcosinate). In a preferred embodiment mixture of alkanoyl glycinate and alkanoyl sarcosinate are used.

As was the case in U.S. application Ser. No. 12/751,049, it is further preferred that surfactant systems contain no more than the maximum amount of specific anionics; or the maximum amount of combined anionic and nonionic (not including components (a) and (b) of our surfactant system).

In particular, the compositions preferably have 3% or less, preferably 2% or less, more preferably 1% or less of any alkyl sulfate anionic including alkyl sulfates such as sodium dodecyl sulfates or alkoxylated sulfates such as lauryl ether sulfate. In a preferred embodiment, the compositions will have 0.2% or less anionic surfactant and, in particular 0.2% or less alkyl sulfate.

Further, in another preferred embodiment, the composition of the invention will comprise 5 to 70% of surfactant system isethionate product; 20 to 85% of surfactant system alkanoyl (as set forth); 20 to 80% of surfactant system amphoteric and/or zwitterionic surfactant and 3% or less anionic and nonionic together (other than the components (a) and (b)).

Other than preferred limitations on alkyl sulfate and preferred limitations in total anionic and nonionic (excluding (a) and (b)), surfactants which can be used are as noted.

The anionic surfactant may be, for example, an aliphatic sulfonates, such as a primary alkane (e.g., $C_8$-$C_{22}$) sulfonates, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

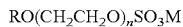

wherein R is an alkyl or alkanoyl having 8 to 18 carbons, preferably 12 to 18 carbons, n has an average value of greater than at least 0.5, preferably between 2 and 3; and M is a solubilizing cation such as sodium, potassium, ammonium or substituted ammonium.

The anionic may also be alkyl sulfosuccinates (including mono- and dialkyl, e.g., $C_6$-$C_{22}$ sulfosuccinates); fatty acyl taurates, fatty acyl amino acids other than lauroyl and cocoyl glycinate or sarcosinate, alkyl sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, and fatty acyl isethionates.

Another class of anionics is carboxylates such as follows:

$R-(CH_2CH_2O)_nCO_2M$ wherein R is $C_8$ to $C_{20}$ alkyl; n is 0 to 10; and M is as defined above.

Another carboxylate which can be used is amido alkyl polypeptide carboxylates such as, for example, Monteine LCQ® by Seppic.

The nonionic surfactants which may be used include in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Preferred alkyl polysaccharides are alkylpolyglycosides of the formula:

$R^2O(C_nH_{2n}O)_t(glycoyl)_x$ wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is form 0 to about 10, preferably 0; and x is from 1.3 to about 10, preferably from 1.3 to about 2.7. The glycosyl is preferably derived from glucose.

The zwitterionic and amphoteric surfactants which are used in preferred embodiments of the invention are as noted below.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

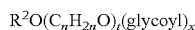

$R^2-Y^{(+)}\underset{\underset{(R^3)_x}{|}}{\phantom{-}}CH_2-R^4Z^{(-)}$ wherein $R^2$ contains an alkyl, alkanoyl, or hydroxyl alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-5-hexadecylsulfonio]-3-hydroxypentane-1-sulfate;
3-[P,P-diethyl-P-3,6,9-trioxatetradexocylphosphonio]-2-hydroxypropane-1-phosphate;

Amphoteric surfactants which may be used in this invention include at least one acid group. This may be a carboxylic or a sulphonic acid group. They include quaternary nitrogen and therefore are quaternary amido acids. They should generally include an alkyl or alkanoyl group of 7 to 18 carbon atoms. They will usually comply with an overall structural formula:

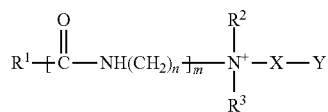

$R^1-\overset{O}{\overset{\|}{C}}-NH(CH_2)_n\!\!\underset{m}{\phantom{-}}\!\!-\overset{R^2}{\underset{R^3}{\overset{|}{\underset{|}{N^+}}}}-X-Y$ where $R^1$ is alkyl or alkanoyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $-CO_2-$ or $-SO_3-$ Alkylamphoacetates and dialkylamphoacetates are also intended to be covered among possible amphoteric compounds which may be used.

Examples of suitable amphoteric surfactants are alkyl betaines; amidoalkyl betaines; amphocarboxylate derivatives such as (mono or di)alkylamphoacetate; and amidoalkyl sultains.

Cocamidopropybetaine, lauramidopropyl betaine, lauryl betaine, coco-betaine, lauroamphoacetate, cocoamphoacetate, cocoamphopropionate, lauryl hydroxysultaine and cocamidopropyl hydroxysultaine surfactants are particularly useful and preferred for this application.

A preferred surfactant system of the invention comprises isethionate product, mixtures of alkanoyl glycinate and alkanoyl sarcosinate and amphoteric surfactant such as betaine. Further, such may be combined with free fatty acids, e.g., $C_8$-$C_{24}$ straight chain free fatty acid such as, for example, lauric acid.

The third required component of the invention is use of 1 to 15%, preferably 5 to 12% by wt. triglyceride oil, preferably soybean oil. These levels are suitable when oil is hydrogenated at level of 40% or less. When levels of hydrogenation are lower, e.g., less than 25%, preferably less than 20%, then triglyceride can be used at levels of 5 to 30%, preferably 10 to 25% by wt.

As seen from the Examples, when the oil is kept in this defined level of hydrogenation, compositions approach rheology of soap (e.g., has squeaky feel of soap) rather than that of syndet and lather is not compromised.

In a third embodiment of the invention, the invention relates to a method of approximating soap-like rheology and consequent soap-like feel of a composition containing a surfactant system comprising 5 to 70% by wt. fatty acyl isethionate and 2 to 5% by wt. alkanoyl surfactant(s) which method comprises adding to said composition 1 to 15% of a triglyceride wherein the degrees of hydrophobic of said triglyceride is 40% or less.

Protocol

Lather Generation Protocol

Add 1 millimeter (ml) of sample to syringe barrel (60 ml);
Add 9 ml water;
Mix sample in syringe resulting in 1/10 dilution in syringe;
Extend plunger to 50 ml to obtain 10 ml of fluid and 40 ml of air;
Shake syringe 10 times; and
Inject and eject the plunger 6 times.

Lather Stability Protocol

Measured by monitoring turbidity of lather using a Diffusing Wave spectroscopy (DWS) set-up. One measures transport means free path (1*) which is among other things, a function of bubble size where lower 1* signifies smaller bubble size and greater lather stability. See also D. A. Weitz and D. J. Pine, Diffusing Wave Spectroscopy, Dynamic Light Scattering, edited by W. Brown (Oxford University Press, Oxford, 1992), which reference is hereby incorporated by reference into the subject application.

EXAMPLES

Example 1

In order to more clearly show how degree of hydrogenation affects the slope of dimensionless shear stress over dimensionless shear rate, applicants plotted a graph showing, on X axis, dimensionless shear rate when $Ca=(\mu R_{32} \, d\gamma/dt)/\sigma$, and, on Y axis, dimensionless shear stress $(\tau_w R_{32})/\sigma$, where Ca is the capillary number, $\mu$ is the viscosity of the bulk phase, $R_{32}$ is the volume-surface radius of bubbles, $\sigma$ is the surface tension and $\tau_w$, is the wall stress. Tested synthetic detergent surfactant based compositions ("syndet") comprised liquid composition with acyl isethionate product and alkanoyl surfactant as part of surfactant system (defined as "Base"), where the base contained either 10% or 20% oil (where oil is hydrogenated to various degrees as noted in the Table below). Applicants further plotted on the graph soap composition ("soap Perfect Whip" from Shiseido) and "Syndet Lux Splash" whose formulations are set forth below. Applicants measured and set forth the following information relating to slope values in the Tables below:

| | Slope |
|---|---|
| "Soap Perfect Whip" from Shiseido (formulation set forth below) | 0.25 |
| "Syndet Lux Splash" (formulation set forth below) | 0.42 |
| Base w/o oil | 0.26 |
| 10% soy oil samples | |
| Degree of hydrogenation (%) | |
| 0 | 0.253 |
| 25 | 0.265 |
| 100 | 0.292 |
| 20% soy oil samples | |
| Degree of hydrogenation (%) | |
| 0 | 0.239 |
| 25 | 0.256 |
| 35 | 0.275 |
| 50 | 0.476, 0.589, 0.292 (wide variation in this data since the lather created is very bad and not reproducible) |

As seen from the above Table, baseline slope for a soap composition ("Soap Perfect Whip" from Shiseido was 0.25 and, for syndet composition, slope was 0.42. The formulation for soap, syndet and base without oil are set forth below:

| Base Formulation | |
|---|---|
| Ingredient | % by Wt. |
| Sodium cocoyl glycinate | 4.00 |
| Betaine | 4.80 |
| Fatty acyl isethionate product | 2.00 |
| Lauric acid | 3.00 |
| Sodium cocoyl satcosinate | 1.00 |
| Glycerin | 10.00 |
| Acrylate/methacrylate polymer (e.g., Carbopol ® Aqua SF-1) | 1.20 |
| NaOH | 0.10 |
| Water | Balance |

When above formulation comprises oil, the water is reduced and replaced by amount of oil used.

| Syndet "Lux Splash" Formulation | |
|---|---|
| Ingredient | Active % in Formula |
| Deionized water | 78.30 |
| Cocoamidopropylbetaine | 5.67 |
| Sodium $C_{12}$-$C_{13}$ pareth sulfate | 12.86 |
| Ethylenediaminetetracetic acid | 0.10 |
| Glycerin | 2.00 |
| Antimicrobial (e.g., hydantoin) | 0.10 |
| Perfume and minors | 0.97 |

Soap Formulation (from ingredient label of "Soap Perfect Whip", Japanese product made by Shiseido).

| Ingredient |
|---|
| Water |
| Potassium Stearate |
| PEG (-600) |
| Potassium myristate |
| Glycerine |
| Potassium laurate |
| Dipropylene glycol |
| Stearic acid |
| Butylene glycol |
| Glyceryl stearate |
| Myristic acid |
| Lauric acid |
| Polyquaternium-7 |
| Beeswax |
| Phytosteryl/octyldodecyl lauroyl glutamate |
| Terrasodium EDTA |
| Perfume |

The above is an example of soap composition (e.g., having one synthetic surfactant). This is an example of a composition associated with "squeaky feel" sensation referred to in the specification.

It can be seen from the Table above summarizing slope values that, for base composition with 10% soybean sample, when degree of hydrogenation is 40% or less (0 or 25 hydrogenation), slope is closer to the slope of soap, thereby indicating a more soap-like rheology which, in turn, is associated with "squeaky" feel consumer perception.

More particularly, a slope of 0.25 is indicative of soap-like rheology (a function of immobile interfaces) while a slope of 0.4 is indicative of rheology for synthetic surfactant based liquid (due to more mobile interfaces between bubbles). See, for example, Denkov et al., J. Colloids & Surfaces A 263, page 29 (2005) entitled "Wall Slip and Viscous Dissipation in Sheared Foams: Effect of Surface Mobility". A copy of the reference is hereby incorporated by reference into the subject application. In particular, the slope is a measure of the mobility or lack of mobility of the interfaces between bubbles, and having a slope approaching that of soap is a likely indicator of a "squeaky" feel. A synthetic surfactant based composition (with higher measured slope) provides a more "slimy" feel compared to soap. In the base with 10% soy sample where soy had 100% hydrogenation (certainly >40%), rheology is less soap-like (slope of 0.292) and the slope approaches that of the syndet composition.

Where soybean sample is higher (20% oil), it is preferable the degree of hydrogenation be less than 25%, preferably less than 20% to be closer to slope of soap (and have more soap-like rheology). Higher hydrogenation amounts of 35% and 50% have slopes closer to that of syndet than to that of soap.

Example 2

In order to show the effect of excessive hydrogenation on lather stability, applicants measured transport mean free path (1*) in millimeters (y axis) versus time over 600 seconds α-axis). The area under the curve for sample with no oil and for 10%, 20% and 30% samples (no hydrogenation in any) were set forth in Table below.

| Sample | Area under curve (10-580 s) mm-s | Liquid Oil (wt %) | Hydrogenated Oil (wt %) |
| --- | --- | --- | --- |
| Without oil | 522.5 | 0 | 0 |
| 10% oil | 568.5 | 10 | 0 |
| 20% oil | 620.4 | 20 | 0 |
| 30% oil | 637.8 | 30 | 0 |

The table indicates that lather decay process is substantially not affected by the presence of 10-30% soybean oil compared to sample with no oil, as long as there was no hydrogenation.

Applicants then measured compositions containing 10% or 25% soybean oil where oil was hydrogenated and information is set forth in Table below:

| Sample | Area under curve (10-580 s) mm-s | Liq. Oil (wt %) | Hydrog. Oil (wt %) |
| --- | --- | --- | --- |
| Without soybean oil | 522.5 | 0 | 0 |
| 10% soybean oil | 568.5 | 10 | 0 |
| 10% oil with 25% hydrogenation | 676.6 | 7.5 | 2.5 |
| 10% oil with 35% hydrogenation | 571.5 | 6.5 | 3.5 |
| 10% oil with 50% hydrogenation | 808.5 | 5 | 5 |
| 10% oil with 100% hydrogenation | 1064.7 | 0 | 10 |

| Sample | Area under curve (10-580 s) mm-s | Liq. Oil (wt %) | Hydrog. Oil (wt %) |
| --- | --- | --- | --- |
| Without soybean oil | 522.7 | 0 | 0 |
| 20% soybean oil | 620.4 | 20 | 0 |
| 20% oil with 25% hydrogenation | 828.4 | 15 | 5 |
| 20% oil with 35% hydrogenation | 936.2 | 13 | 7 |

As seen from area under curve measurements in these tables, for 10% soybean oil when degree of hydrogenation reached 50%, the area under curve was 808.5 indicating rapid lather degradation (larger bubbles over shorter times). When degree of hydrogenation was 40% or less, stability was fine (e.g., area under curve of less than 830, preferably 700 or less).

In 20% soybean oil sample, less hydrogenation leads to lather destabilization. Accordingly, the degree of hydrogenation must be kept lower (less than 25%, preferably less than 20%) when more triglyceride is used.

The invention claimed is:

1. Cleansing composition that approaches squeaky clean skin feel of soap comprising:
   1) 1 to 30% surfactant system comprising:
      a) 5 to 70% by wt. surfactant system of a fatty acyl isethionate product wherein, 40 to 80% of the product comprises fatty acyl isethionate and 15 to 50% of the product comprises free fatty acid and/or fatty acids salt/soap
      b) 20 to 85% by wt. surfactant system of an alkanoyl surfactant or surfactants, wherein alkyl group on alkanoyl is $C_8$ to $C_{20}$
   2) 1 to 15% triglyceride wherein degree of hydrogenation is 40% or less.

2. Composition according to claim 1 comprising 2 to 25% of surfactant system.

3. Composition according to claim 1 comprising 30 to 75% by wt. alkanoyl surfactant as component 1(b).

4. Composition according to claim 1, wherein alkanoyl surfactant is selected from the group consisting of alkanoyl glycinate, alkanoly sarcosinate and mixtures thereof.

5. A composition according to claim 1 comprising 5 to 12% by wt. triglyceride.

6. A composition according to claim 1, wherein triglyceride comprises soybean oil.

7. A composition according to claim 1 wherein the degree of hydrogenation is 1 to 35%.

8. A composition according to claim 1 which has lather stability defined by plotting transport mean free path (y axis) versus time over 600 seconds (x axis) and measuring area under curve, and wherein said area under curve is less than 830 mm times seconds.

9. A cleansing composition that approaches squeaky clean skin feel of soap comprising:
   1) 1 to 30% surfactant system comprising:
      a) 5 to 70% by wt. surfactant system of a fatty acyl isethionate product wherein, 40 to 80% of the product comprises fatty acyl isethionate and 15 to 50% of the product comprises free fatty acid and/or fatty acids salt/soap.

b) 20 to 85% by wt. surfactant system of an alkanoyl surfactant or surfactants, wherein alkyl group on alkanoyl is $C_8$ to $C_{20}$ 2) 5 to 30% triglycerides wherein degree of hydrogenation less than 25%.

10. A composition according to claim 1 wherein degree of hydrogenation is less than 20%.

11. A method of enhancing soap like rheology and soap-like feel of a composition containing a surfactant system comprising acyl isethionate and alkanoyl surfactant(s) which method comprises adding to such composition 1 to 15% of a triglyceride wherein degree of hydrogenation of said triglyceride is 40% or less.

* * * * *